(12) United States Patent
Fritz et al.

(10) Patent No.: US 11,014,860 B2
(45) Date of Patent: May 25, 2021

(54) METHOD AND SYSTEM FOR PRODUCING OLEFINS

(71) Applicant: LINDE AKTIENGESELLSCHAFT, Munich (DE)

(72) Inventors: Helmut Fritz, Munich (DE); Mathieu Zellhuber, Martinsried (DE); Anton Wellenhofer, Hohenschäftlarn (DE); Martin Schubert, Munich (DE); Florian Winkler, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 21 days.

(21) Appl. No.: 16/347,517

(22) PCT Filed: Oct. 20, 2017

(86) PCT No.: PCT/EP2017/076894
§ 371 (c)(1),
(2) Date: May 3, 2019

(87) PCT Pub. No.: WO2018/082945
PCT Pub. Date: May 11, 2018

(65) Prior Publication Data
US 2019/0284112 A1 Sep. 19, 2019

(30) Foreign Application Priority Data
Nov. 3, 2016 (EP) .................... 16197156

(51) Int. Cl.
*C07C 5/48* (2006.01)
*F25J 3/02* (2006.01)

(52) U.S. Cl.
CPC ............... *C07C 5/48* (2013.01); *F25J 3/0219* (2013.01); *F25J 3/0247* (2013.01); *F25J 2200/02* (2013.01); *F25J 2220/42* (2013.01)

(58) Field of Classification Search
CPC ......... C07C 5/48; C07C 11/04; F25J 2200/02; F25J 2200/80; F25J 2205/04;
(Continued)

(56) References Cited

U.S. PATENT DOCUMENTS

2016/0326070 A1* 11/2016 Winkler ................ C07C 5/48

FOREIGN PATENT DOCUMENTS

| EP | 2716622 A1 | 4/2014 |
|---|---|---|
| WO | WO 2015113747 A1 | 8/2015 |

OTHER PUBLICATIONS

PCT/EP2017/076894 English translation of International Search Report and Written Opinion dated Jan. 16, 2018, 7 pages.
PCT/EP2017/076894 English translation of International Preliminary Report on Patentability dated May 7, 2019, 6 pages.
(Continued)

*Primary Examiner* — Sharon Pregler
(74) *Attorney, Agent, or Firm* — Lathrop GPM LLP (57) ABSTRACT

A process for producing one or more olefins is proposed in which a reaction input containing one or more paraffins is formed and in which a portion of the paraffin(s) present in the reaction input is converted by oxidative dehydrogenation into the olefin(s) to obtain a process gas, wherein the process gas contains at least the olefin(s), the unconverted paraffin(s), oxygen and carbon monoxide and wherein at least a portion of the process gas is subjected to a low temperature separation in which at an operating pressure level one or more gas fractions enriched in oxygen and carbon monoxide compared to the process gas are formed. It is provided that in the low temperature separation in the formation and/or for the conduction of the or at least one of the gas fractions one or more containers and/or one or more conduits having a burst pressure of at least ten times the operating pressure level are used and that the container or at least one of the containers via the or at least one of the conduits is connected to one or more heat exchangers, wherein a total length of the (Continued)

or of the at least one conduit between the or the at least one container and the heat exchanger(s) is not more than fifty times the internal diameter of said conduit. A corresponding plant (100) likewise forms part of the subject matter of the invention.

19 Claims, 2 Drawing Sheets (58) Field of Classification Search
CPC .. F25J 2210/12; F25J 2215/62; F25J 2220/42; F25J 2290/12; F25J 2290/90; F25J 3/0219; F25J 3/0238; F25J 3/0247; F25J 3/0261; F25J 3/0295
See application file for complete search history.

(56) References Cited

OTHER PUBLICATIONS

Eurasian Patent Application No. 201990950/31 English translation of Office Action dated Jul. 17, 2020, 3 pages.
Eurasian Patent Application No. 201990950/31 Office Action dated Jul. 17, 2020, 3 pages.
GOST 31441.1-2011 Non-electrical equipment for potentially explosive atmospheres. Part 1. General requirements; Feb. 15, 2013; 63 pages.
GOST 32569-2013 Industrial steel pipe-lines. Requirements for design and operation in explosive and chemically dangerous industries; Jan. 1, 2015; 159 pages.

\* cited by examiner

METHOD AND SYSTEM FOR PRODUCING OLEFINS

The invention relates to a process for producing olefins and a corresponding plant according to the preambles of the independent claims.

PRIOR ART

Oxidative dehydrogenation (ODH) of paraffins having two to four carbon atoms is known in principle. In ODH the recited paraffins are reacted with oxygen to afford inter alia olefins of identical carbon number and water.

ODH may be advantageous compared to established processes for producing olefins such as steamcracking or catalytic dehydrogenation. For instance, there is no thermodynamic equilibrium limitation on account of the exothermicity of the reactions involved. The formation energies $\Delta G$ for ethane, propane and n-butane are −102, −115 and −118 kJ/mol respectively. ODH may employ comparatively low reaction temperatures. Regeneration of the employed catalysts is in principle not necessary since the presence of oxygen allows an in situ regeneration. Finally, compared to steamcracking smaller amounts of worthless byproducts such as coke are formed.

For further details concerning ODH reference is made to the relevant technical literature, for example Ivars, F. and López Nieto, J. M., Light Alkanes Oxidation: Targets Reached and Current Challenges, in: Duprez, D. and Cavani, F. (ed.), Handbook of Advanced Methods and Processes in Oxidation Catalysis: From Laboratory to Industry, London 2014: Imperial College Press, pages 767-834, or Gärtner, C. A. et al., Oxidative Dehydrogenation of Ethane: Common Principles and Mechanistic Aspects, ChemCatChem, vol. 5, no. 11, 2013, pages 3196 to 3217.

The invention is hereinbelow described in particular having regard to ODH of ethane (so-called ODH-E). However, the use of said invention is in principle possible and advantageous also for ODH of higher paraffins such as propane and butane.

To ensure sustainable activity of the catalysts in ODH a minimum content of oxygen at the reactor outlet is required to avoid reduction of the catalyst and thus a loss in performance thereof. It is therefore generally not possible to operate with a complete oxygen conversion in the reactor. Furthermore, at higher conversions appreciable quantities of carbon monoxide and carbon dioxide are formed as byproducts which similarly to the remaining oxygen are thus present in the process gas from the reactor and in separating steps arranged downstream of the ODH must be separated off from the primary product(s) and other byproducts.

As also elucidated hereinbelow it is possible that in the separation of lower boiling fractions from higher boiling fractions carbon monoxide and oxygen in particular undesirably undergo enrichment beyond concentrations that are a safety concern.

The present invention has for its object to improve corresponding processes and plants and in particular to address the problem of enrichment of carbon monoxide and oxygen in a corresponding separation in ODH, in particular in ODH-E.

DISCLOSURE OF THE INVENTION

Against this background, the present invention proposes a process for producing olefins and a corresponding plant having the features of the dependent claims. Embodiments are in each case subject matter of the dependent claims and of the description which follows.

Material streams, gas mixtures etc. may in the context of the present usage be rich or poor in one or more components, wherein the indication "rich" may represent a content of not less than 95%, 96%, 97%, 98%, 99%, 99.5%, 99.9% or 99.99% and the indication "poor" may represent a content of not more than 5%, 4%, 3%, 2%, 1% 0.5%, 0.1% or 0.01% on a molar, weight or volume basis. If a plurality of components are reported the indication "rich" or "poor" relates to the sum of all components. If reference is made for example to "oxygen" or "ethane" a pure gas or else a mixture rich in the respective component may be concerned.

Material streams, gas mixtures etc. may in the context of the present usage also be "enriched" or "depleted" in one or more components, wherein these terms are based on a content in a starting mixture. They are "enriched" when they contain not less than 1.5 times, 2 times, 5 times, 10 times, 100 times or 1000 times the content, and "depleted" when they contain not more than 0.75 times, 0.5 times, 0.1 times, 0.01 times or 0.001 times the content, of one or more components based on the starting mixture.

The terms "pressure level" and "temperature level" are used hereinbelow to characterize pressures and temperatures, these being intended to express that pressures and temperatures need not be present in the form of exact pressure/temperature values. A pressure level or temperature level may for example be within ±1%, 5%, 10%, 20% or 50% of a mean value. A plurality of pressure and temperature levels may represent disjoint or overlapping ranges. The same pressure/temperature level may for example still be present even when pressures and temperatures have been reduced on account of transmission losses or cooling. Pressure levels reported here in bar are absolute pressures.

A "rectification column" is in the context of the present usage a separating unit adapted for at least partly fractionating a substance mixture introduced in gaseous or liquid form or in the form of a biphasic mixture having liquid and gaseous fractions, optionally also in the supercritical state, by rectification, i.e. respectively generating from the substance mixture pure substances or at least substance mixtures having different compositions. Rectification columns are typically configured as cylindrical metal containers provided with internals, for example separating trays or ordered or unordered packings. A rectification column comprises a bottoms evaporator. This is a device having a heat exchanger which is heated and adapted for heating a liquid fraction accumulating in the bottom of the rectification column, also known as bottoms liquid. By means of a bottoms evaporator a portion of the bottoms product is continuously evaporated and recycled in gaseous form into the separating region.

ADVANTAGES OF THE INVENTION

As recited at the outset a typical process gas formed by ODH contains not only primary products such as olefins (and typically carboxylic acids which are co-formed in particular when using certain catalysts) but also inter alia unconverted paraffins, oxygen, carbon monoxide and carbon dioxide. The process gas typically also contains water and optionally relatively small amounts of inert gases. A separation arranged downstream of the ODH must therefore separate off the byproducts from the desired primary product(s)/the unconverted paraffins.

Separation is typically effected, as also illustrated with reference to the accompanying FIG. 1, after a compression of the process gas. Said process gas is then typically freed by means of a water quench at least of large parts of any carboxylic acids present and of the water present. This is followed by scrubbing steps for removing carbon dioxide.

The process gas now still containing essentially olefins, the unconverted paraffins, oxygen and carbon monoxide and also smaller amounts of inert gases is freed of residual water and precooled. A staged condensation of the process gas is then effected in a subsequent low temperature separation. The remaining gas fractions are in each case supplied to the next condensation step. The condensates are separated in a low temperature rectification, wherein in turn a gas fraction and a liquid fraction are formed. The gas fraction from the low temperature rectification is typically combined with the gas fraction remaining downstream of the last condensation step to afford a further gas fraction, the so-called fuel gas fraction/tail gas fraction, and typically sent to a thermal recovery. The liquid fraction from the low temperature rectification is subjected to further separating steps.

The fuel gas fraction typically comprises at least the predominant part of the carbon monoxide and oxygen present in the process gas supplied to the low temperature separation and of the remaining components which boil lower than the desired olefins. The desired olefins are at least predominantly transferred into the liquid fraction from the low temperature rectification, together with the higher boiling unconverted paraffins.

Owing to the nature of the condensative/distillative derivation of the gas fractions in the low temperature separation these undergo increasing enrichment with oxygen and carbon monoxide without any additional measures. A typical process gas supplied to the low temperature separation contains for example about 36 mol % of ethane, 37 mol % of ethylene, 20 mol % of carbon monoxide, 4 mol % of oxygen and 1 mol % of inert components. "Inert components" is hereinbelow to be understood as meaning components which are not reactive in ODH nor condensable under the conditions used, including the classical inert gases such as nitrogen and argon but also for example methane which likewise exhibits inert behaviour in ODH. In this case, even after a first condensation step in which the process gas is cooled to −53° C. at about 20.4 bar, the remaining gas fraction contains about 44 mol percent of carbon monoxide and 8 mol percent of oxygen. This gas mixture already markedly exceeds both the explosion threshold and the oxygen threshold concentration (see below). Generally even an oxygen fraction of 3000 vppm at the reactor outlet can have the result that a gas mixture formed in the low temperature rectification has carbon monoxide and oxygen fractions of 66 vol % and 13 vol % respectively.

The (lower) explosion threshold of a gas indicates the content in a gas mixture above which ignition/explosion is possible at simultaneously sufficient oxygen content. For carbon monoxide said threshold is at a content of markedly over 10 mol percent and is influenced inter alia by the content of hydrogen and water in the gas mixture considered in each case. Under standard conditions said threshold is reported as 12.5 mol percent. In the elucidated gas fractions formed in a typical low temperature separation downstream of an ODH the content of carbon monoxide is at least 40 and up to 70 mol percent, as also elucidated with reference to accompanying FIG. 2 and just recited, and the explosion threshold has therefore been markedly exceeded.

When the explosion threshold has been exceeded an explosion may take place provided that the so-called oxygen threshold concentration has also been exceeded. This indicates the oxygen content above which an explosion can occur. In other words for an explosion to be possible both the explosion threshold and the oxygen threshold concentration must have been exceeded.

The oxygen threshold concentration for carbon monoxide is extremely low and is approximately half of that of methane and approximately equal to that of ethylene. In mixtures of different flammable gas components intermediate values are typically established. In the present case, i.e. the gas mixtures formed in the low temperature separation, the oxygen threshold concentration is at a value of about 6 mol percent provided that no further measures are adopted. Explosions and possibly even detonations can therefore occur in principle.

The explosion thresholds of gases may be determined according to standardized methods corresponding to relevant standards such as DIN 51649-1 oder EN 1839. The explosion thresholds for numerous flammable gases and vapours in air under standard conditions are listed in extensive tabulated works and databases. For nonatmospheric conditions and likewise for mixtures of different gases an extrapolation from known values may be effected or a calculation based on known prescriptions may be performed. For further details reference is made to the technical literature, for example Markus, D., and Maas, U., Die Berechnung von Explosionsgrenzen mit detaillierter Reaktionskinetik, Chemie Ingenieur Technik, vol. 76, no. 3, 2004, and the references cited therein. The same applies for the determination of oxygen threshold concentrations.

An explosion is an uncontrolled deflagration of an ignitable gas mixture with a laminar flame front. Explosions and detonations are distinguished essentially by the rate of propagation. In an explosion said rate is below the speed of sound and in a detonation said rate is typically markedly above the speed of sound. Explosions and detonations of gas mixtures in containers result in a massive pressure increase which can result in bursting of the containers and corresponding secondary damage. For stoichiometric air/hydrocarbon mixtures a maximum pressure increase during an explosion by a factor of 10 may be calculated. The effects of a detonation are markedly graver. Here, the pressure increase factor may be 50 or more. After a certain run-up distance and a minimum concentration of fuel and oxygen an explosion can transition into a detonation.

The present invention solves these problems in a process for producing one or more olefins in which a reaction input containing one or more paraffins is formed and in which a portion of the paraffin(s) present in the reaction input is converted by oxidative dehydrogenation into the olefin(s) to obtain a process gas, wherein the process gas contains at least the olefin(s), the unconverted paraffin(s), oxygen and carbon monoxide and wherein at least a portion of the process gas is subjected to a low temperature separation in which at an operating pressure level one or more gas fractions enriched in oxygen and carbon monoxide compared to the process gas are formed, when in the low temperature separation in the formation and/or for the conduction of the or at least one of the gas fractions one or more containers and/or one or more conduits having a burst pressure of at least ten times the operating pressure level are used, and by means of the further measures elucidated hereinbelow.

The operating pressure level describes the pressure level employed in the low temperature separation in regular operation which may be 10 to 30 bar for example. A "burst pressure" is hereinbelow to be understood as meaning in particular a calculated burst pressure determined for example from material and construction data and/or a test pressure and/or a mechanical design pressure (for explosion-resistant design).

A "reaction input" is in the context of the present usage the entire gas mixture which is subjected to ODH. This may in particular also be supplied to the reactor(s) used in the form of separate material streams. For example a paraffin-containing material stream and an oxygen-containing material stream may be combined to afford a corresponding reaction input in the reactor(s) used or upstream of the reactor(s).

In the context of the present invention at least a portion of the containers and conduits in which relevant gas fractions having a high oxygen content and carbon dioxide content are present thus have an explosion-resistant design. As recited, during an explosion of the recited gas fractions a pressure increase of not more than a factor of 10 typically takes place. The measures proposed in accordance with the invention ensure that despite the composition of relevant gas fractions and even upon explosion thereof damage to the pressure-bearing components of a corresponding plant can no longer occur and/or no release of relevant gas fractions or combustion products thereof to the environment takes place. In this way process engineering measures such as addition of inertization agents or the configuration of the separation means and the use of explosion arresters may be at least partly eschewed.

As already elucidated above a relevant "gas fraction" is to be understood here as meaning in particular a gas mixture which is enriched in oxygen and carbon monoxide compared to the process gas and is formed in a low temperature separation. An outflow of a gas mixture formed upstream of the low temperature separation, for example in a water quench or a carbon dioxide removal, is thus not a gas fraction in this context since it is not formed in the low temperature separation. Relevant gas fractions are generated in particular in the recited condensation steps and the downstream low temperature rectification of the derived condensates. The elucidated fuel gas fraction is also a gas fraction formed in the low temperature separation.

It is known from the prior art, for avoidance of explosions, for example to avoid enrichment of oxygen and/or flammable components in relevant gas fractions and thus to monitor the content of relevant components continuously. A relevant gas fraction may be discarded and/or the upstream separation may be performed less sharply to avoid the described concentration. This results in a reduced total yield since product is co-discarded.

By contrast, in the context of the present invention the explosion-resistant design increases the total yield. In the context of the present invention it is not necessary for all containers and/or conduits in which explosive gas fractions are present to be explosion resistant. Limitation to those containers and/or conduits exposed to a higher explosion risk than others is also possible.

In the case of long pipelines and/or containers (i.e. when a free route available for propagation of an explosion and made up of the pipeline length and optionally of the container length corresponds to at least 50 times the internal diameter) the explosion of a hydrocarbon/oxygen mixture can transition into a detonation because a sufficient run-up length is then present. This applies in particular when appropriate stoichiometric ratios (lambda of one, ideal mixture) are present. According to the prior art in petrochemistry in pressurized systems the transition of an explosion into a detonation is prevented for example by provision of internals, introduction of dumped beds, installation of explosion protection filters, implementation of pipelines as bundles, installation of extinguishing systems (dust) and use of liquid curtains. Common to all these solutions is that the explosion is brought to a halt by a high mass coupled with small gap widths and large surface areas. The propagating flame is cooled and is ideally eventually extinguished. Common to all these measures are small gap widths coupled with a large surface area. All of these measures result in increased capital costs, operating costs and maintenance costs.

In the present invention a detonation is avoided by keeping relevant conduits and/or containers sufficiently short. It was in particular recognized in this connection that the heat exchangers employed in the recited low temperature separation, to which relevant conduits are connected, can be configured as explosion arresters or inherently constitute effective explosion arresters. It is therefore provided in accordance with the invention that at least one of the containers via the or at least one of the conduits is connected to one or more heat exchangers, wherein a total length of the or of the at least one conduit between the or the at least one container and the heat exchanger(s) is not more than fifty times the internal diameter of said conduit. The recited conduits and/or containers advantageously further have an explosion-resistant design but on account of the reduced conduit length detonation resistance advantageously need not be produced.

The present invention makes it possible in particular to reduce the degree of dilution in the process, in particular the dilution with low-boiling components such as methane or nitrogen, compared to the prior art. This allows the economy of a corresponding process to be optimized in terms of both running costs and capital costs.

The running costs are achieved in particular by an increased energy efficiency of the process on account of the reduced amount of ballast material in the form of diluents and an increased yield. The increased yield likewise results from the reduced amount of diluents. Because these are present in smaller amounts the removal thereof results in lower losses of products of value. In a known demethanizer, i.e. a separating column used for removal of methane and lower boiling compounds, these products of value go overhead to a lesser extent when overall a smaller amount of light gases need be removed. Furthermore, the separation effort in the bottom of a corresponding separating column required to produce on-specification ethylene is reduced, thereby resulting in a reduced risk of contamination to the product. This results in an altogether higher yield coupled with improved energy efficiency and increased security of supply for downstream processes.

The savings in terms of capital costs brought about by the markedly reduced construction sizes/volumes in the low temperature separation and all upstream plant parts which are possible in the context of the present invention greatly outweigh the additional cost and complexity for the safety engineering safeguarding proposed in accordance with the invention.

A process configured according to the present invention/a correspondingly implemented plant benefits from compact process management and a similarly compact construction. This is a result inter alia of the measure that explosion-resistant design is applied in the field of low temperature separation and having regard to length-limited conduits. The small additional cost and complexity for the increased design pressure is achieved in particular since, due to reduced dilution, the mass and volume flows in the explosion-endangered region are markedly lower than in the prior art and the explosion-resistant design is undertaken exclusively in the low temperature part in which low temperatures and relatively high pressures prevail and thus the volume flows are markedly smaller compared to those in other plant parts. The cross-sectional areas of the conduits and apparatuses are therefore comparatively small, thus simplifying dimensioning for high design pressures. The limitation of conduit lengths undertaken in accordance with the invention further improves compactness and has the additional result that the design pressure need be stipulated merely for the case of an explosion and not for a detonation.

All in all the use of the present invention allows large parts of the plant to be configured and operated in a more advantageous fashion because a comparatively small part of the plant is implemented with the greatest possible compactness and strength. When considering conventional plants such a course of action is not obvious since it is not foreseeable that a selective modification of one part of the plant can result in such a great technical and economic advantage for the overall plant. In developing conventional plants those skilled in the art would wish to avoid under all circumstances the obtainment of explosive mixtures in the cryogenic high-pressure separation part of the plant.

It is thus of particular advantage when the heat exchanger(s), to which the or the at least one conduit whose total length between the or the at least one container and the heat exchanger(s) is not more than fifty times the internal diameter of said conduit is connected, have an explosion propagation-inhibiting configuration. A corresponding heat exchanger may for example have an explosion propagation-inhibiting configuration when an effective slot dimension is kept small when, such as in conventional internals, dumped beds, explosion protection filters etc., an explosion is brought to a halt by a high mass coupled with small slot widths and a large surface area. The propagating flame is also cooled in a corresponding heat exchanger and is eventually extinguished. The explosion propagation-inhibiting configuration of a heat exchanger is therefore also based on the use of small slot dimensions coupled with a large surface area.

To choose a suitable slot dimension those skilled in the art employ for example the known standard slot widths published for a multiplicity of gases or gas mixtures. The standard slot width is the largest width of a 25 mm long slot which under predetermined test conditions safely prevents a gas mixture ignited in an instrument from igniting through the slot a gas mixture located outside the instrument. Corresponding standard slot widths may readily be transferred/converted to the slot dimensions used for heat exchangers. A corresponding heat exchanger is advantageously explosion resistant, i.e. it has a burst pressure of at least 10 times the operating pressure level. In this way an explosion can occur without it being able to transition into a detonation and result in damage.

It is further of particular advantage when conduits which conduct gases or biphasic mixtures and are connected to containers in which condensates are separated enter submerged, i.e. terminate under the desired liquid level. The traversing gas thus bubbles through a liquid, thereby integrating a liquid explosion arrester into the container.

It is further of particular advantage when column internals are implemented as oriented packings or dumped beds, thereby integrating an explosion arrester into the column function.

It is further of particular advantage when the total gas volume contained in the column is divided by at least one rectification tray into a plurality of gas volumes separated from one another by liquid and optionally solid internals (for example downcomer walls), thus integrating a liquid explosion arrester into the column function. This may be effected for example by an or at least the one single- or multi-flow crossflow rectification tray.

The present invention may also be advantageously employed in the manner elucidated above when in the low temperature separation in the formation and/or for the conduction of the or at least one of the gas fractions one or more further containers and/or one or more further conduits are used and the container or at least one of the further containers via the or at least one of the further conduits is connected to one or more further heat exchangers but a total length of the or of the at least one further conduit between the or the at least one further container and the further heat exchanger(s) is more than fifty times the internal diameter of said conduit. Particularly in explosion-critical environments a corresponding conduit may in this case be provided with an explosion arrester to prevent propagation of the explosion and transition into a detonation. Corresponding conduits may also be implemented as detonation-resistant conduits. A corresponding conduit then has a burst pressure of at least 50 times the operating pressure level.

In the context of the present invention in particular a low temperature separation as already elucidated above may be employed. The low temperature separation thus advantageously comprises multiple and stepwise cooling of the process gas, wherein after each cooling a condensate is separated from the process gas and one of the gas fractions remains and at least a portion of the gas fractions is supplied to a further cooling. As recited, in these gas fractions in particular a corresponding enrichment can occur and the containers and conduits containing/conducting corresponding gas fractions are therefore advantageously implemented as recited. In other words to separate at least one of the condensates the container or at least one of the containers are used and to supply at least one of the gas fractions to the further cooling the or one of the conduits are used.

The invention likewise provides a plant for producing one or more olefins adapted for forming a reaction input containing one or more paraffins, comprising a reaction unit adapted for converting by oxidative dehydrogenation a portion of the paraffin(s) present in the reaction input into the olefin(s) to obtain a process gas, wherein the process gas contains at least the olefin(s), the unconverted paraffin(s), oxygen and carbon monoxide and comprising a low temperature separation adapted for forming at an operating pressure level one or more gas fractions enriched in oxygen and carbon monoxide compared to the process gas.

Such a plant has the feature that in the low temperature separation for formation and/or for conduction of the or at least one of the gas fractions one or more containers and/or one or more conduits having a burst pressure of at least ten times the operating pressure level are provided and that the container or at least one of the containers via the or at least one of the conduits is connected to one or more heat exchangers, wherein a total length of the or of the at least one conduit between the or the at least one container and the heat exchanger(s) is not more than fifty times the internal diameter of said conduit.

For features and advantages of a corresponding plant reference is made to the above elucidations concerning the features and advantages of the process. In particular such a plant is adapted for performing a process according to the specific embodiments elucidated above and comprises means suitable therefor. In this regard too reference is made to the above intimations.

The invention is more particularly elucidated below with reference to the appended drawings which illustrate inter alia preferred embodiments of the present invention.

DETAILED DESCRIPTION OF THE DRAWINGS

In the figures that follow functionally or structurally equivalent elements are indicated with identical reference numerals and for the sake of simplicity are not repeatedly elucidated. When plant parts are described hereinbelow the elucidations concerning these also apply correspondingly to the process steps implemented by means of these plant parts and vice versa.

Figure 1:
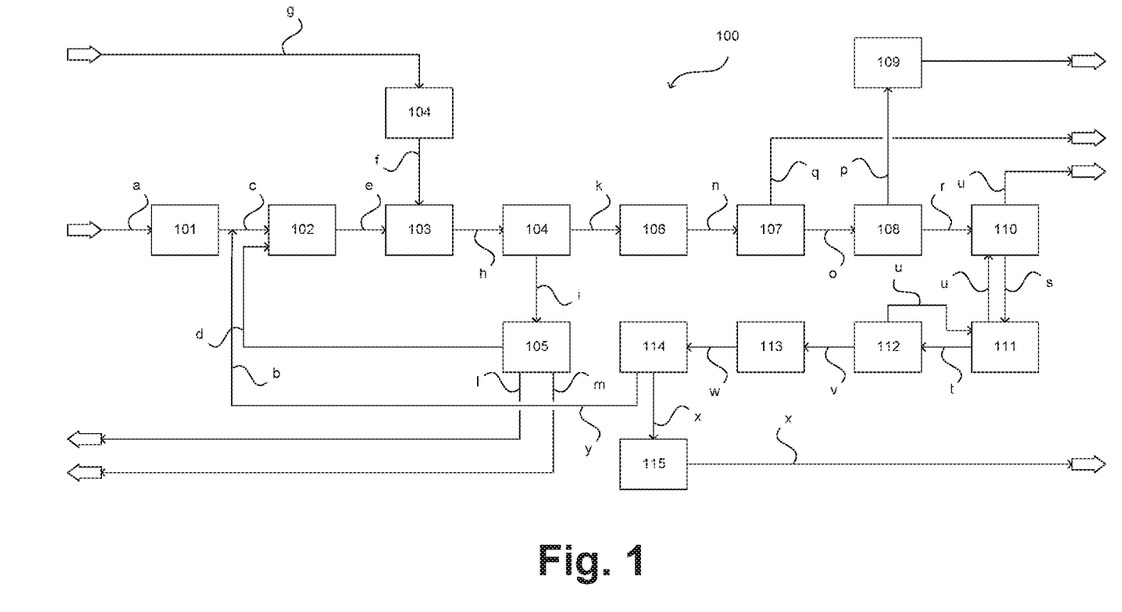
FIG. 1 illustrates a plant for producing olefins according to one embodiment of the invention.

In FIG. 1 a plant for producing olefins according to one embodiment of the invention in the form of a greatly simplified plant diagram is illustrated and collectively referred to as 100. Notwithstanding that a plant 100 for ODH of ethane (ODH-E) is described below, the present invention is also suitable, as recited, for use in ODH of higher hydrocarbons. In this case the elucidations which follow apply accordingly.

In the plant 100 a separation input in the form of a material stream a is supplied to a rectification unit 101 having for example one or more rectification columns and subjected to a rectification. In the depicted example the separation input contains at least ethane and higher hydrocarbons, in particular corresponding higher paraffins. The rectification unit 101 may also be supplied with one or more further separation inputs, for example the material stream b shown here and more particularly elucidated below.

In the rectification unit 101 the separation input is subjected to a rectification alone or together with the further separation input(s) to obtain a gas mixture which contains ethane but is poor in higher hydrocarbons. The gas mixture is withdrawn in the form of a material stream c and supplied to a preheating unit 102. In the preheating unit 102 the gas mixture is preheated, wherein in the depicted example the preheating unit 102 is also supplied with a water or steam stream d. Further material streams may also be supplied, as is illustrated here in the form of a material stream b. Further obtained in the rectification unit 101 is a component mixture containing predominantly or exclusively the higher hydrocarbons. Said mixture is not shown explicitly.

A material stream e outflowing from the preheating unit 102 is supplied to a reaction unit 103 to form a reaction input. On account of its formation using the separated product from the rectification unit 101 the reaction input contains ethane but is poor in higher hydrocarbons. The reaction input may further contain one or more diluents such as water or inert gases and further components. These may also be supplied to the reaction unit 103 in the form of further material streams (not shown).

In the depicted example the reaction unit 103 is supplied with an oxygen-containing material stream f. This may be provided using an air separation plant 104. To this end the air separation plant 104 is supplied with an airstream g. The oxygen-containing material stream f may be substantially pure oxygen but fractions of nitrogen and of noble gases may also be present depending on the operation of the air separation plant 104. In this way it is likewise possible to supply diluent.

Outflowing from the reaction unit 103 is a process gas in the form of a process gas stream h which contains ethylene formed in the reaction unit 103 by ODH of a portion of the ethane in the reaction input. The product mixture further contains acetic acid likewise formed from ethane during ODH in the reaction unit 103, water, carbon monoxide, carbon dioxide, unconverted oxygen and the diluent(s) and further compounds if added or previously formed in the reaction unit 103.

It will be appreciated that reaction unit 103 may comprise a or else a plurality of reactors which are for example operated in parallel. In the latter case these reactors are each supplied with corresponding reaction inputs, which may have identical or different compositions, and corresponding oxygen-containing material streams f and in each case corresponding process gas streams h are formed. The latter may for example be combined and supplied together as process gas to the units elucidated below.

The process gas is transferred into a quench unit 104 in which, for example in a quench column, it may be contacted with quench water or a suitable aqueous solution. In the quench unit 104 the process gas is in particular cooled and the acetic acid formed in the reaction unit 103 is scrubbed out of the process gas. Acetic acid-laden process water outflows from the quench unit 104 in the form of a material stream i, the process gas at least largely freed of acetic acid outflows from the quench unit 104 in the form of a material stream k.

In an optional acetic acid recovery unit 105 acetic acid is separated off from the acetic acid-laden process water as glacial acetic acid which is discharged from the plant 100 as material stream I. Pure process water likewise recovered in the acetic acid recovery unit 105 may be supplied to the preheating unit 102 in the form of the previously elucidated material stream d. The process water supplied to the reactor may also be provided partly or fully in the form of externally supplied freshwater. Water that is no longer usable or required may be discharged from the plant 100 and supplied to a wastewater treatment in the form of a wastewater stream m.

The process gas present in the form of material stream k and at least largely freed of acetic acid is compressed to a suitable pressure level, for example 15 to 25 bar, in a compressing unit 106 and in the form of a compressed material stream n supplied to an amine scrub unit 107. Scrubbed out therein are in particular portions of the carbon dioxide present in the process gas. After regeneration of the amine the scrubbed-out carbon dioxide may be discharged from the plant in the form of a material stream q. The process gas thus partly freed of carbon dioxide is transferred in the form of a material stream o into a lye scrub unit 108 and further purified of carbon dioxide therein. Generated in the lye scrub unit 108 is waste lye which in the form of a material stream p may be transferred into a waste lye treatment unit 109 and finally discharged from the plant 100.

The process gas further purified in the lye scrub unit 108 is transferred in the form of a material stream r into a pre-cooling and drying unit 110 where it may be freed from residual water in particular. The dried process gas is transferred in the form of a material stream s into a low temperature unit 111 and subsequently in further-cooled form in the form of one or more material streams t into a demethanization unit 112. In the low temperature unit 111 and the demethanization unit 112 components lower boiling than ethylene, in particular carbon monoxide and oxygen, are separated off from the process gas, wherein the remainder stays in condensed form. If the process gas contains higher hydrocarbons formed as a byproduct during ODH in the reaction unit 103 these are likewise converted into condensate.

The separated-off components lower boiling than ethylene are recycled in the form of one or more material streams u through the low temperature unit 111 and the precooling and drying unit 110, therein optionally combined with further corresponding material streams, used for cooling purposes and discharged from the plant 100. If required the hydrocarbons having two and optionally more carbon atoms are supplied in the form of a material stream v to a hydrogenation unit 113 in which in particular acetylene likewise formed as byproduct during ODH in the reaction unit 103 may be hydrogenated. After the hydrogenation the material stream now referred to as w is transferred into an ethylene removal unit 114. Details of a usable low temperature unit 111 and of a usable demethanization unit 112 are more particularly illustrated in FIG. 2.

In the ethylene removal unit 114 ethylene is at least largely separated off from other components and in the form of a material stream x after utilization in an ethylene cooling unit 115 may be discharged from the plant 100 in gaseous form. The remaining components, predominantly ethane and optionally higher hydrocarbons, are withdrawn in the form of a material stream y. If higher hydrocarbons are present therein these are advantageously recycled into the reaction unit in the form of the previously recited material stream b. An optional workup of this material stream b may be effected.

Figure 2:
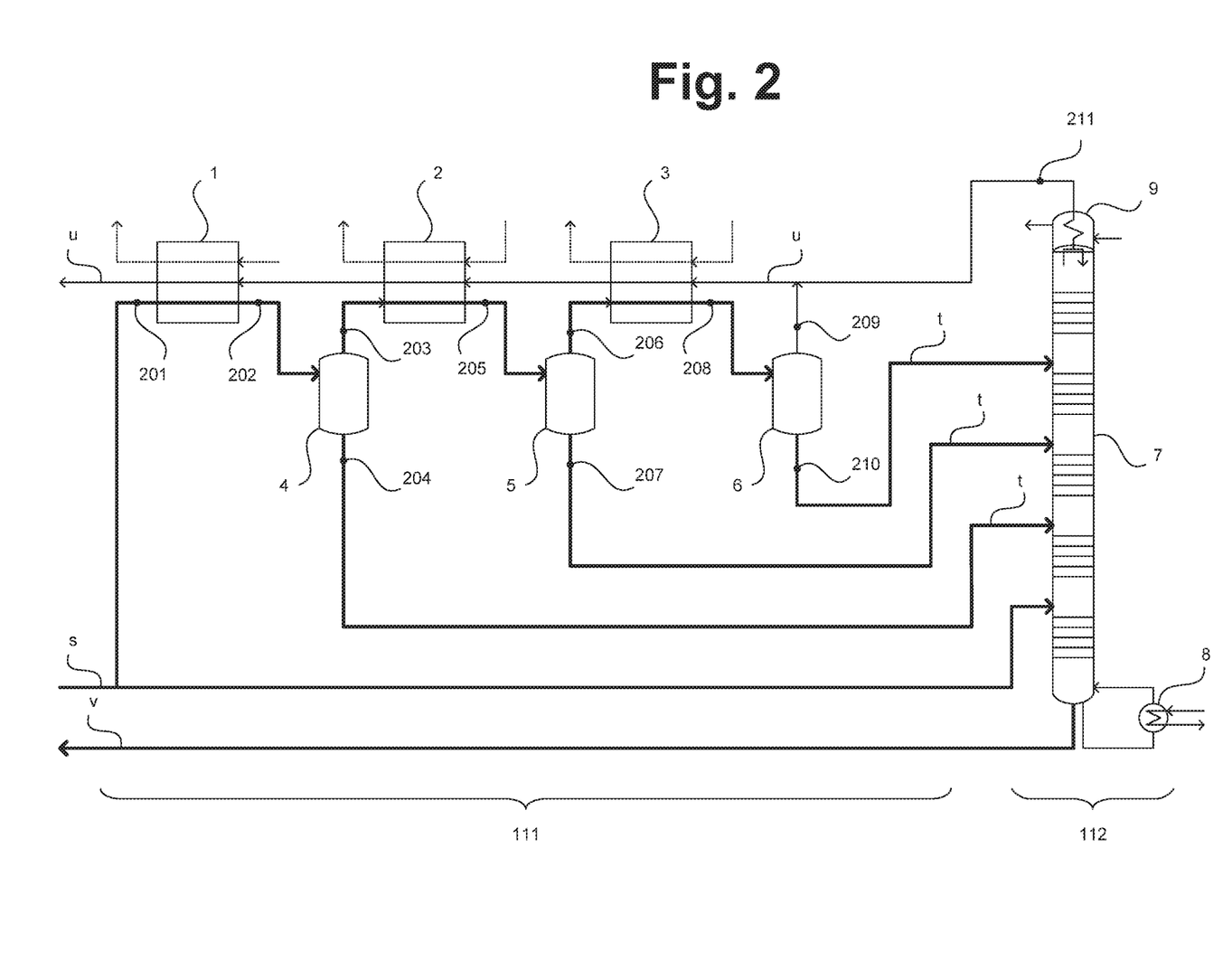
FIG. 2 illustrates a rectification unit for use in a plant for producing olefins according to one embodiment of the invention.

FIG. 2 shows a low temperature unit and a demethanization unit for use in a plant for producing olefins according to one embodiment of the invention. The low temperature unit and the demethanization unit may for example be employed in a plant 100 such as is shown in FIG. 1 and are therefore as summarized with 111 and 112 therein. The material streams s, t, u and v previously depicted in FIG. 1 are also shown here. The depiction of the respective elements is not true to position and not true to scale.

The partially condensed process gas is supplied in the form of the material stream s to the low temperature unit 111. The gaseous portion of the process gas is successively passed through heat exchangers 1 to 3 and therein cooled to ever lower temperature levels. The heat exchangers 1 to 3 are cooled with ethylene streams (shown as dashed lines) to this end (high-pressure ethylene in heat exchanger 1, medium-pressure ethylene in heat exchanger 2, low-pressure ethylene in heat exchanger 3). Additionally used for cooling is material stream u which in the depicted example contains the components of the process gas lower boiling than ethane or, more generally, lower boiling than paraffins having N carbon atoms which are separated off in the low temperature unit 111 and the demethanization unit 112.

Downstream of the heat exchangers 1 to 3 the process gas/a biphasic mixture formed in each case by cooling in the heat exchangers 1 to 3 is in each case transferred into separators 4 to 6 where in each case a condensate is separated from the process gas. The condensates are introduced into a rectification column 7 of the demethanization unit 112, the so-called demethanizer, at a height corresponding to their composition of matter. Furthermore, the fraction of the process stream s previously condensed in the precooling is introduced into the rectification column 7 directly. A separation of liquid and gaseous proportions of the process stream s before introduction may also be effected.

A bottoms evaporator 8 of the rectification column 7 is heated using propane for example, a tops condenser 9 is cooled using low-pressure ethylene for example. The rectification column 7 is operated such that predominantly the components lower boiling than ethylene undergo enrichment at its top and the heavier compounds undergo enrichment at its bottom. In this way a portion of the material stream u may be withdrawn from the top of the rectification column 7 and the material stream v may be withdrawn from the bottom of the rectification column 7. A fraction of the process gas remaining in gaseous form in the separator 6 may likewise be used in the formation of the material stream u.

Tables 1 and 2 which follow depict typical parameters of a selection of the material streams shown in FIG. 2 at positions 201 to 211 of the low temperature unit 111 and the demethanization unit 112, such as are obtained without supplying further gases as elucidated above.

The process gas introduced in the form of the material stream s comprises in the depicted example at position 201 not only the contents of carbon monoxide and oxygen reported in Table 2 but also 36 mol percent of ethane, 37 mol percent of ethylene and 1 mol percent of argon. Contained in the gas mixture withdrawn from the top of the rectification column 7 at position 211 are not only the contents of carbon monoxide and oxygen reported in Table 2 but also 10 mol % of ethylene and 4 mol % of argon. The reported values are typical illustrative values.

TABLE 1

| Position | Pressure | Temperature |
| --- | --- | --- |
| 201 | 20.4 bar | −31° C. |
| 202 | 20.2 bar | −53° C. |
| 205 | 19.9 bar | −76° C. |
| 208 | 19.7 bar | −97° C. |
| 211 | 18.8 bar | −97° C. |

TABLE 2

| Position | Carbon monoxide | Oxygen | Throughput |
| --- | --- | --- | --- |
| 201 | 20 mol % | 4 mol % | 3 t/h |
| 203 | 44 mol % | 8 mol % | 1.2 t/h |
| 204 | 3.8 mol % | 0.8 mol % | 1.2 t/h |
| 206 | 62 mol % | 11 mol % | 0.8 t/h |
| 207 | 5 mol % | 1.3 mol % | 0.4 t/h |
| 209 | 72 mol % | 13 mol % | 0.7 t/h |
| 210 | 8 mol % | 2 mol % | 0.1 t/h |
| 211 | 64 mol % | 13 mol % | 2.6 t/h |

As is evident from Table 2 without supplying further gases as elucidated above the oxygen content reaches a value which, with the carbon monoxide present, already affords an explosive mixture at position 203.

The present invention provides that in the low temperature separation in the formation and/or for the conduction of the or at least one of the gas fractions one or more containers and/or one or more conduits having a burst pressure of at least ten times the operating pressure level are used. Such conduits may be for example the containers 4 to 6 and the conduits at the positions 201 to 211 which, as recited, can conduct explosive gas mixtures. The rectification column 7 advantageously likewise has an explosion-resistant design.

The invention claimed is:

1. Process for producing one or more olefins in which a reaction input containing one or more paraffins is formed and in which a portion of the paraffin(s) present in the reaction input is converted by oxidative dehydrogenation into the olefin(s) to obtain a process gas, wherein the process gas contains at least the olefin(s), the unconverted paraffin(s), oxygen and carbon monoxide and wherein at least a portion of the process gas is subjected to a low temperature separation in which at an operating pressure level one or more gas fractions enriched in oxygen and carbon monoxide compared to the process gas are formed, characterized in that, in the low temperature separation, in the formation of the one or more gas fractions and/or for the conduction of the one or more gas fractions, one or more containers and/or one or more conduits having a burst pressure of at least ten times the operating pressure level are used, and that the container or at least one of the containers is connected, via the conduit or at least one of the conduits, to one or more heat exchangers, wherein total length of the conduit(s) between the container(s) and the heat exchanger(s) is not more than fifty times the internal diameter of said conduit(s), wherein the burst pressure is a mechanical design pressure.

2. Process according to claim 1, in which the heat exchanger(s), to which the or the at least one conduit whose total length between the or the at least one container and the heat exchanger(s) is not more than fifty times the internal diameter of said conduit is connected, have an explosion propagation-inhibiting configuration.

3. Process according to claim 2, in which the explosion propagation-inhibiting configuration of the heat exchanger(s) comprises the use of a maximum slot dimension tailored to the gas fraction(s).

4. Process according to claim 2, in which the heat exchanger(s) having an explosion propagation-inhibiting configuration have a burst pressure of at least ten times the operating pressure level.

5. Process according to claim 1, in which in the low temperature separation in the formation and/or for the conduction of the or at least one of the gas fractions one or more further containers and/or one or more further conduits are used, wherein the container or at least one of the further containers via the or at least one of the further conduits is connected to one or more further heat exchangers, wherein a total length of the or of the at least one further conduit between the or the at least one further container and the further heat exchanger(s) is more than fifty times the internal diameter of said conduit.

6. Process according to claim 5, in which the or the at least one further conduit whose total length between the or the at least one further container and the further heat exchanger(s) is more than fifty times the internal diameter has a burst pressure of at least fifty times the operating pressure level.

7. Process according to claim 5, in which the or the at least one further conduit whose total length between the or the at least one further container and the further heat exchanger(s) is more than fifty times the internal diameter comprises an explosion arrester.

8. Process according to claim 1, in which an at least partly gaseous fluid is conducted through the or at least one of the conduits and introduced into the container or at least one of the containers, wherein in the or the at least one container a liquid is separated from the fluid and the or the at least one conduit opens into the or the at least one container below a liquid level of the liquid.

9. Process according to claim 1, in which the low temperature separation comprises the use of a rectification column comprising at least one oriented packing and/or dumped bed.

10. Process according to claim 1, in which the low temperature separation comprises the use of a rectification column comprising at least one rectification tray which divides the total gas volume contained in the column into a plurality of gas volumes separated from one another by liquid and optionally solid internals.

11. Process according to claim 1, in which the low temperature separation comprises multiple and stepwise cooling of the process gas, wherein after each cooling a condensate is separated from the process gas and one of the gas fractions remains and at least a portion of the gas fractions is supplied to a further cooling.

12. Process according to claim 11, in which to separate at least one of the condensates the container or at least one of the containers is used and/or to supply at least one of the gas fractions to the further cooling the or one of the conduits is used.

13. Plant (100) for producing one or more olefins adapted for forming a reaction input containing one or more paraffins, comprising a reaction unit (103) adapted for converting by oxidative dehydrogenation a portion of the paraffin(s) present in the reaction input into the olefin(s) to obtain a process gas, wherein the process gas contains at least the olefin(s), the unconverted paraffin(s), oxygen and carbon monoxide and comprising a low temperature separation adapted for forming at an operating pressure level one or more gas fractions enriched in oxygen and carbon monoxide compared to the process gas, characterized in that in the low temperature separation for the formation and/or for the conduction of the or at least one of the gas fractions one or more containers and/or one or more conduits having a burst pressure of at least ten times the operating pressure level are provided and that the container or at least one of the containers via the or at least one of the conduits is connected to one or more heat exchangers, wherein a total length of the or of the at least one conduit between the or the at least one container and the heat exchanger(s) is not more than fifty times the internal diameter of said conduit.

14. Process according to claim 3, in which the heat exchanger(s) having an explosion propagation-inhibiting configuration have a burst pressure of at least ten times the operating pressure level.

15. Process according to claim 2, in which the burst pressure is a calculated burst pressure and/or a test pressure and/or a mechanical design pressure.

16. Process according to claim 3, in which the burst pressure is a calculated burst pressure and/or a test pressure and/or a mechanical design pressure.

17. Process according to claim 4, in which the burst pressure is a calculated burst pressure and/or a test pressure and/or a mechanical design pressure.

18. Process according to claim 6, in which the or the at least one further conduit whose total length between the or the at least one further container and the further heat exchanger(s) is more than fifty times the internal diameter comprises an explosion arrester.

19. Process according to claim 2, in which an at least partly gaseous fluid is conducted through the or at least one of the conduits and introduced into the container or at least one of the containers, wherein in the or the at least one container a liquid is separated from the fluid and the or the at least one conduit opens into the or the at least one container below a liquid level of the liquid.

* * * * *